United States Patent [19]

Swanson

[11] Patent Number: 4,812,739
[45] Date of Patent: Mar. 14, 1989

[54] APPARATUS AND METHOD FOR USING MICROWAVE RADIATION TO MEASURE WATER CONTENT OF A FLUID

[76] Inventor: Claude V. Swanson, 1800 Old Meadow Rd., Suite 220, McLean, Va. 22102

[21] Appl. No.: 906,952

[22] Filed: Sep. 15, 1986

[51] Int. Cl.$^4$ .............................................. G01R 27/04
[52] U.S. Cl. ............................ 324/58.5 A; 324/58 A
[58] Field of Search .......... 324/58.5 A, 58 A, 58.5 R; 73/61 R, 61.1 R, 73

[56] References Cited

U.S. PATENT DOCUMENTS

| | | | |
|---|---|---|---|
| 3,246,145 | 4/1966 | Higgins . | |
| 3,498,112 | 3/1970 | Howard . | |
| 3,693,979 | 9/1972 | Walker . | |
| 3,851,244 | 11/1974 | Mounce | 324/58.5 A |
| 4,193,027 | 3/1980 | Wyslouzil | 324/58.5 R |
| 4,289,020 | 9/1981 | Paap . | |
| 4,301,400 | 11/1981 | Paap | 324/58.5 A |
| 4,326,163 | 4/1982 | Brook | 324/58.5 A |
| 4,352,288 | 10/1982 | Paap et al. . | |
| 4,423,623 | 1/1984 | Ho et al. . | |
| 4,458,524 | 7/1984 | Meador et al. . | |
| 4,484,133 | 11/1984 | Riggin | 324/58.5 A |

Primary Examiner—Reinhard J. Eisenzopf
Assistant Examiner—Anthony L. Miele
Attorney, Agent, or Firm—Marks Murase & White

[57] ABSTRACT

A microwave system for determining the volume fraction of water in a fluid. In the described application, the fluid is crude oil, and the system is used to determine the volume fraction of water in the crude oil. First and second microwave beams, differing in frequency, reception location, or both, are transmitted through the liquid, and respective absorption losses are calculated. The volume fraction of water is determined according to the absorption losses. Different reception locations are used to detect the passage of a large slug of water.

20 Claims, 3 Drawing Sheets

APPARATUS AND METHOD FOR USING MICROWAVE RADIATION TO MEASURE WATER CONTENT OF A FLUID

BACKGROUND OF THE INVENTION

The present invention relates to method and apparatus for using microwave radiation to measure the volume fraction and/or spatial distribution of a first fluid in a mixture of that fluid and a second fluid such as an oil-water mixture. It is especially useful for measuring water infiltration in a crude oil pipeline.

A multitude of devices are used to measure the water content of oil or other organic fluids, with special attention being paid to the measurement of the water content of crude oil. These devices find special utility when used as monitors on oil pipelines or oil loading pipes used for loading oil tankers. In general, they measure water content by measuring the attenuation due to absorption of a single microwave beam transmitted across a conduit carrying the oil. They are intended to detect and measure water which is dispersed in the oil in the form of a homogenous distribution of fine droplets. For example, U.S. Pat. No. 4,301,400 to Hans J. Paap, U.S. Pat. No. 4,289,020 also to Hans J. Paap, and U.S. Pat. No. 3,498,112 to D. D. Howard disclose such devices. It is a known embellishment on these devices to use gamma radiation in conjunction with the single microwave beam in order to obtain a more accurate and reliable measurement of water content.

As mentioned, these devices are in general useful only for determining the volume fraction of water which is dispersed in oil as fine droplets, and not for detecting the presence of large "slugs" or globules or water which may be present in a pipeline. This is a disadvantage in systems where it is necessary to detect such large globules of water to prevent costly damage to equipment, For example, large slugs of water could devastate refinery equipment.

SUMMARY OF THE INVENTION

The present invention is preferably embodied in a device having a microwave generator which generates two or more microwave beams in the frequency range between 1 and 200 GHz. The device then measures the attenuation of the beams as they propagate through the fluid. The device comprises first means, on one side of a volume of the fluid, for generating first and second microwave beams; second means, arranged across the volume from the first means, for receiving the first and second generated microwave beams after they have been attenuated at least in part by the water in the fluid and for generating at least one signal indicative of degree of attenuation of the first and second microwave beams; and third means, electrically connected to the second means and responsive to the at least one signal, for computing a volume fraction of water in the fluid based on the at least one signal. The two microwave beams differ from each other in at least one characteristic, such as frequency or path through the fluid, or both. The beams may also be differentiated by timing. This device can be generalized to include a plurality of microwave generators and corresponding microwave transmitters arranged in co-extensive linears arrays on either side of the volume.

Here and throughout the specification and claims, the term "mixture" will be applied to any sharing of a given volume by two fluids which maintain their respective physical and chemical identities. Thus, the term is intended to encompass terms such as "suspension" or "sol". It is also intended to cover circumstances wherein a substantially continuous interface exists between the two fluids.

BRIEF DESCRIPTION OF THE DRAWINGS

The features and advantages of the invention described above, as well as others, will be more clearly understood with reference to the drawings, in which.

DETAILED DESCRIPTION OF THE PREFERRED EMBODIMENTS

Figure 1:
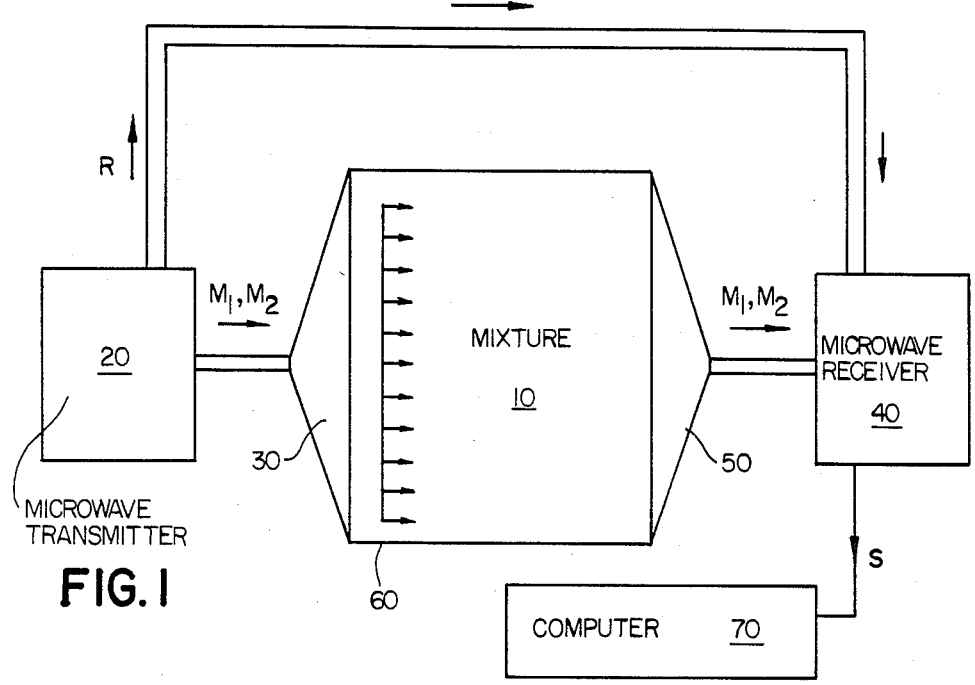
FIG. 1 is a partially schematic block diagram of a first exemplary embodiment of a fluid content measurement device according to the invention.

FIG. 1 is a partially schematic end-on view of an arrangement for measuring the volume fraction of a first fluid in a mixture (as defined above) of that fluid with another fluid, such as an oil-water mixture, according to the present invention. To make the discussion concrete, the arrangement will be described as it would be used in the continuous measurement of crude oil/water mixture flowing through a pipe, with flow being transverse to the plane of the figure. It will be understood, however, that the usefulness and scope of the device is not limited to this specific application.

The volume of oil-water mixture the water content of which is instantaneously being measured in FIG. 1 is designated by numeral 10. On one side of volume 10, the left side in FIG. 1, is first means for generating first and second microwave beams $M_1$ and $M_2$ comprising a microwave transmitter 20 and a transmit horn 30. Arranged across the volume from the first means, on the right-hand side in FIG. 1, is second means for receiving microwave beams $M_1$ and $M_2$ after they have been attenuated at least in part by water in the oil-water mixture 10. These means comprise a microwave receiver 40 and a receive horn 50. Beams $M_1$ and $M_2$ each have a wavefront parallel to line 60. These wavefronts propagate transverse to the flow of the oil-water mixture 10 and are received by receive horn 50. First and second microwave beams $M_1$ and $M_2$ as attenuated in the oil-water mixture 10 are preferably combined with a reference signal R also originating in microwave transmitter 20. Microwave receiver 40 then generates a signal S indicative of the degree of attenuation of beam $M_1$ and beam $M_2$ as compared to reference signal R. Signal S is fed to a computer 70 where it is processed to provide an on-line measurement of the volume fraction of water in oil-water mixture 10.

As mentioned above, there is a reference signal either passed from the generator to the receiver or otherwise provided to the receiver to provide a reference level of the transmitted power. The receiver then measures the received power, from which it is possible to calculate the power absorbed by the mixture in the pipe in a fashion which will now be described.

In an embodiment in which more than one frequency is used, the microwave absorption will be measured at each freuency propagated. For any given frequency, the average absorption of the fluid is:

$$a\nu = \frac{1}{B} \ln \frac{PT\nu}{PR\nu}$$

where:
  $a\nu$ = average absorption at frequency $\nu$;
  $B$ = the distance through the fluid;
  $PR\nu$ = received power corrected for insertion loss, resonance effects, and other distortions; and
  $PT\nu$ = transmitted power.

The water content can be measured by measuring this value at more than one frequency, and taking advantage of the high absorption of water at about 23 GHz, the so-called water absorption line. For example, if three measurements are made, one may be made at the water absorption line frequency and the other measurements can be made at frequencies differing from this frequency by the same amount. The results can then be combined algebraically to derive the volume fraction of water.

For example, let the frequency of the water absorption line be denoted by $\nu_1$, and the other two frequencies by $\nu_1 \pm \Delta\nu$. Assuming the oil absorption at frequency $\nu$, varies linearly with frequency in the form $$ao\nu = ao + ao'(\nu - \nu_1)$$

it can be shown that the volume fraction of water can be derived from these three absorption frequency measurements using the following formula:

$$V_w = \frac{2a\nu_1 - a\nu_2 - a\nu_3}{2a\omega\nu_1 - a\omega\nu_2 - a\omega\nu_3}$$

where
  $V_w$ = the volume fraction of water;
  $a\nu_1$ = average absorption at frequency $\nu_1$;
  $a\nu_2$ = average absorption at frequency $\nu_2$;
  $a\nu_3$ = average absorption at frequency $\nu_3$;
  $a\omega\nu_1$ = absorption of water in droplet form at frequency $\nu_1$;
  $a\omega\nu_2$ = absorption of water in droplet form at frequency $\nu_2$; and
  $a\omega\nu_3$ = absorption of water in droplet form at frequency $\nu_3$.

The advantages of this technique derive from the realization that variations in the absorption of oil will not affect the accuracy of the measurement as long as the variation is smooth. Additional measurements at additional frequencies will provide a more accurate value for water content. In the embodiments described above, the computations can be controlled by a small microcomputer, which calculates and reads out the results instantaneously. The computer can also be easily programmed to integrate the water volume to compute the total water volume passing through the pipe in a given time interval.

The above discussion assumes that the water is dispersed throughout the mixture in the form of small droplets. Where it is contemplated that water will occur not only in droplet form but also in the form of large globules, a different phenomenon may become dominant. This phenomenon will be referred to as "shadowing." The microwave energy impinging on such a slug is absorbed completely in the first fraction of a centimeter, so that the rest of the droplet is ineffective in absorbing microwave energy. Very large droplets, measuring more than a centimeter across, normally settle up in very quickly in storage tanks and do not comprise much of the water on-loaded to a tanker. In oil refineries, however, such slugs of water sometimes measuring a foot or more across can occur in refinery pipes and can cause serious damage to processing equipment.

Figure 2:
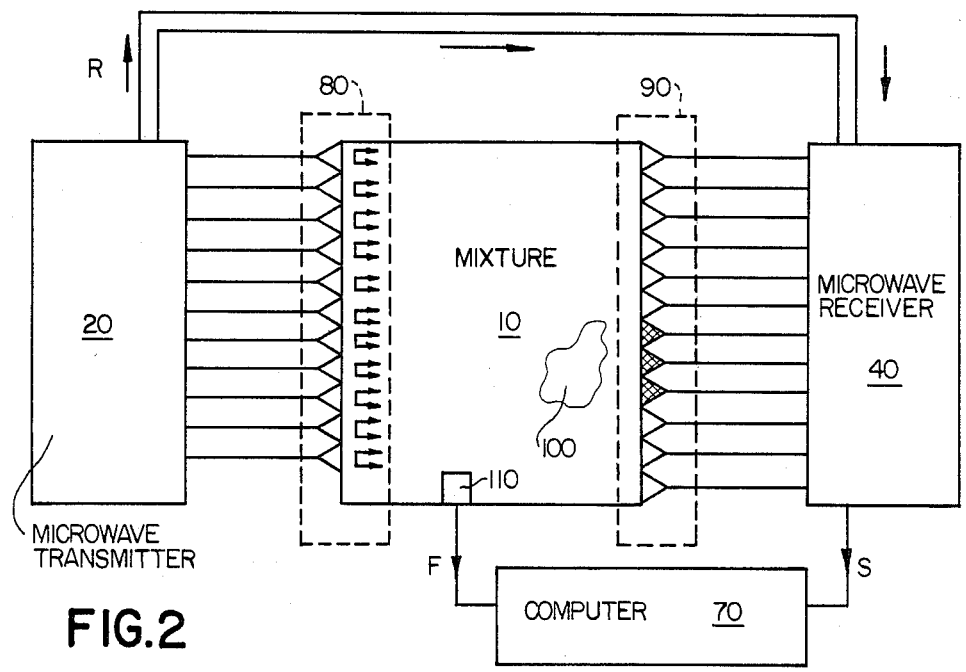
FIG. 2 is a partially schematic block diagram of a fluid distribution measurement device according to a second embodiment of the present invention.

The arrangement of FIG. 2 is intended to cope with these conditions. In FIG. 2, elements and signals have been assigned the designations used to identify their counterparts in FIG. 1. As can be seen, the apparatus in FIG. 2 also includes a microwave transmitter 20 and a microwave receive 40 as well as a computer 70. Transmit horn 30 has, however, been replaced with a linear array 80 of transmit horns. Similarly, receive horn 50 has been replaced by a linear array 90 of receive horns. This arrangement is advantageous in that it can detect the presence of large globules of water, represented in FIG. 2 by irregularly-shaped blot 100. Water globule 100, assuming it is more than a few centimetrs thick in the direction of propagation, will completely absorb any microwave radiation which impinges upon it. Thus, in the embodiment of FIG. 2, the receive horns in linear array 90 "behind" the globule (those which have been cross-hatched in FIG. 2) will be in the "shadow" of globule 100. By determining which of the receive horns in linear array 90 receive microwave radiation, the presence and extent of the water globule 100 can be determined and measured.

Figure 3:
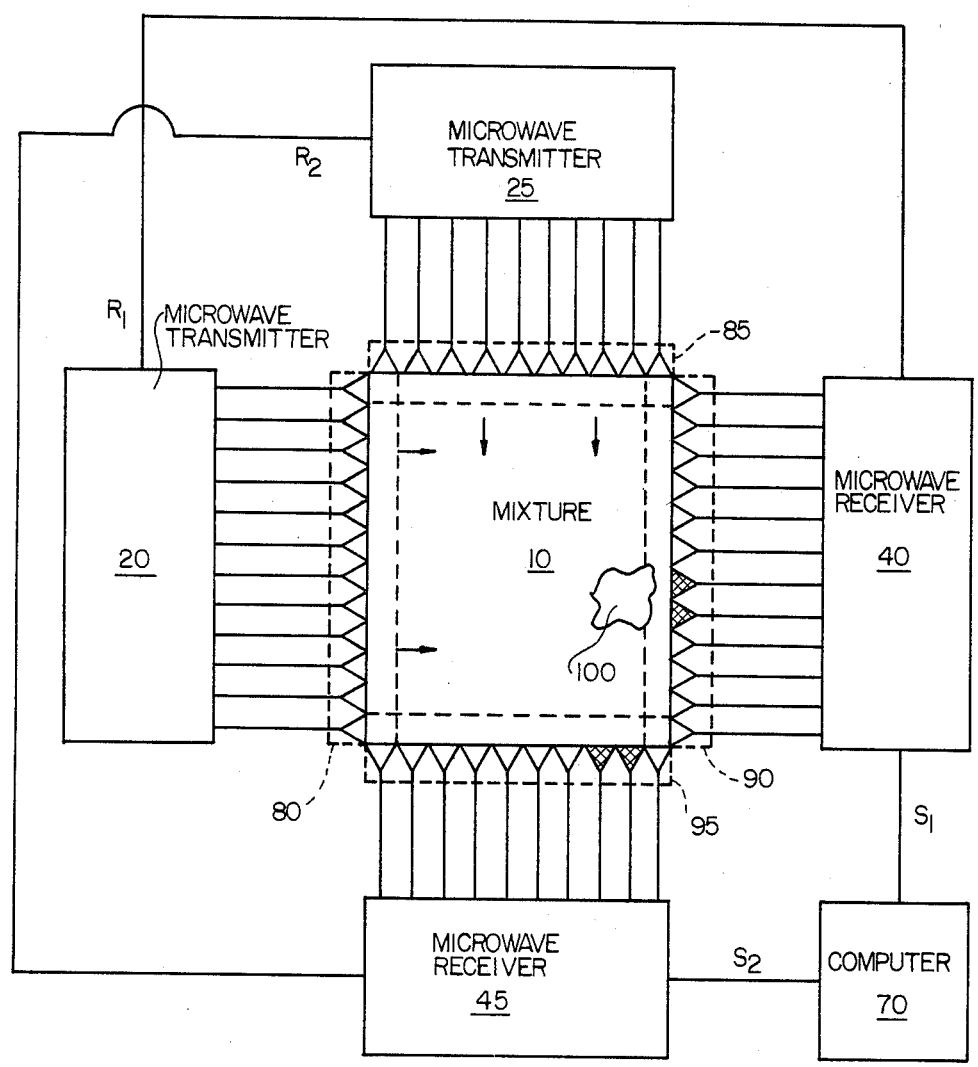
FIG. 3 is a partially schematic block diagram of a fluid distribution measurement device according to a third embodiment of the present invention.

Thus, in the embodiment of FIG. 2, each receiver acts as a sensor and measures absorption along one path through the volume. When a large globule of water crosses some of these paths the measured absorption of those paths will increase many tens of decibels. The dimension of the blob in the direction of the array is obtained from the number of sensors which detect this absorption, i.e., the number of sensors which are in the "shadow." The amount of absorption provides an indicator of the bolb thickness in the beam direction. The length of time the absorption persists multiplied by flow speed in the pipe (measured by flow meter 110 in FIG. 2) provides an approximate measure of the third dimension of the blob. The volume of the blob can be calculated by a small microcomputer attached to the output. This shadowing technique may be made more accurate by using multiple sensors in both the horizontal and vertical axes of the cross plane of the pipe. This is shown in FIG. 3. In the embodiment of FIG. 3, an additional microwave transmitter 25 and an additional microwave receiver 45, with associated horn arrays 85 and 95, respectively, have been added. These additional components obtain the projection or shadow of water globule 100 in a direction perpendicular to the projection obtained by microwave transmitter 20 and microwave receiver 40. The details of adaptation to this two-dimensional system are straightforward and will be apparent to one having ordinary skill in the art.

Figure 4:
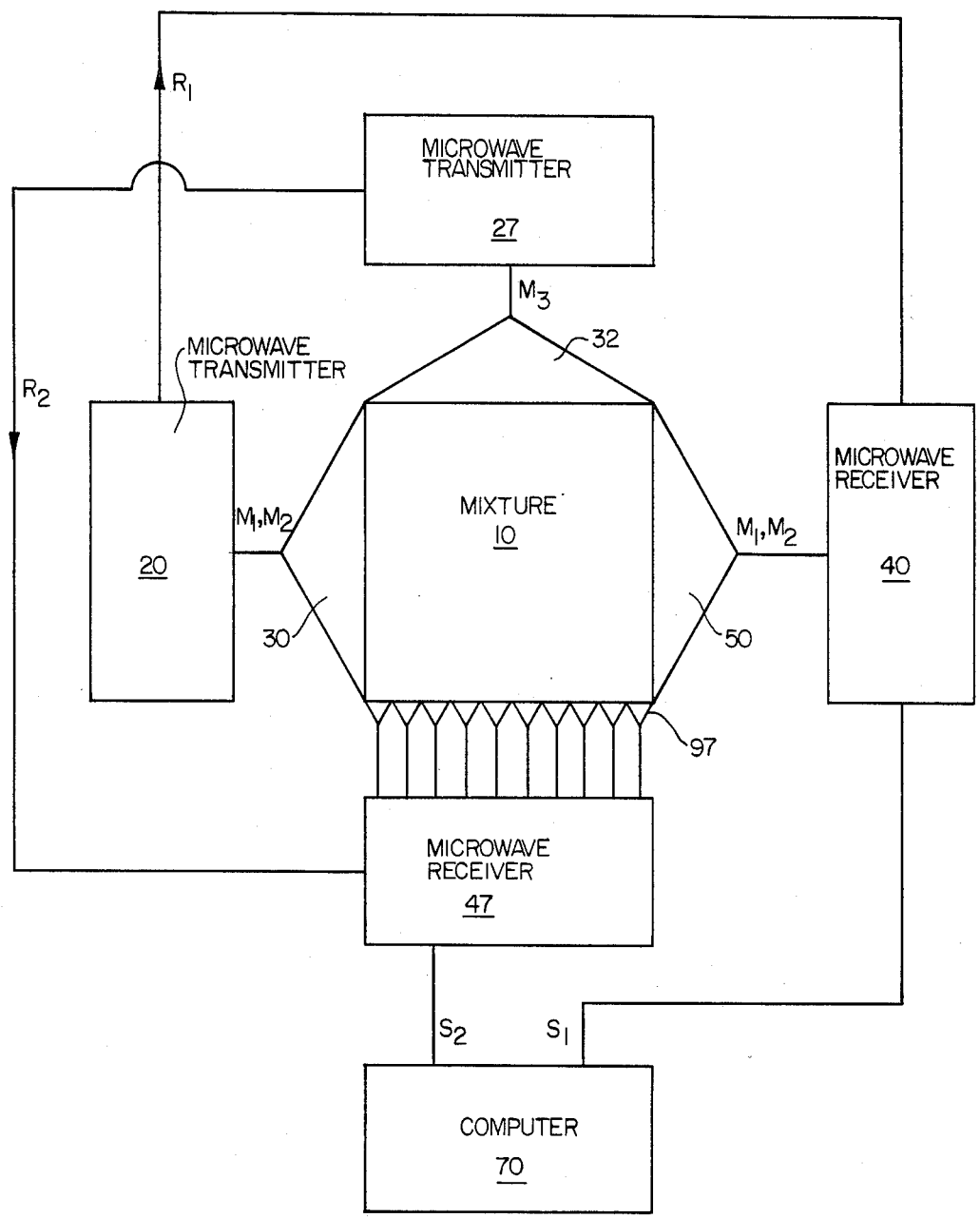
FIG. 4 is a partially schematic block diagram of a fluid content/distribution measurement device according to a fourth embodiment of the present invention.

The embodiment shown in FIG. 4 has both a broad-beam transmitter 20 transmitting two beams $M_1$ and $M_2$ as well as a linear array 97 of receive horns receiving a broad beam transmitted by transmitter 27 through antenna 32. The combination of components 20, 30, 50, 40 defines an apparatus such as that described in connection with FIG. 1 which provides data on the volume fraction of water in mixture 10. The combination of components 27, 32, 97, and 70 defines an apparatus giving information on the existence and location of large globules of water. The embodiment of FIG. 4 thus provides comprehensive data on the amount and distribution of water in mixture 10. It will be apparent to one having ordinary skill that the two combinations can be arranged so that their beams are parallel rather than transverse as shown in FIG. 4.

As described above, the microwave transmission system has two facets, one using at least two broad and coincident microwave beams of different frequencies, and a second using multiple narrow beams. The broad beams measure the average water content in the pipe, so that the device using them is most accurate when the water is dispersed in fine droplets, i.e., where the droplets are on the order of half a centimeter or so. The narrow beam system computes a microwave absorption along each of many paths. Misidentification of the broad beams as the spatially-differentiated narrow beams is avoided by assigning frequencies to the broad beams which are different from frequencies assigned to the narrow beams. Misidentification can also be avoided by pulsing the broad and narrow beams out of phase with each other. The narrow beams may be differentiated by focusing antennae.

The embodiment in FIG. 1 would probably prove most useful in tanker on-loading monitors, while detection systems using multiple beams such as those of FIGS. 2 and 3 would have primary application in petroleum refineries, where large water globules could cause significant damage.

A device such as that shown in FIG. 4 would provide the ultimate in practical, accurate monitoring device. It would be flexible enough to measure water and air content in oil pipelines in a variety of applications in which it is not possible to do so now. For example, it is contemplated that the present invention will be very useful in the measurement and detection of multiphase flow in pipelines. Such a situation commonly occurs in pipelines in which water, oil, air, and/or other fluids occur in globules or strata. When this occurs, presently available monitors are not capable of measuring the fluid properties correctly. A device constructed according to the present invention would not have this disadvantage. Other applications might include use in nuclear power plants or in other pressure steam systems in which two phase flow occurs involving steam and condensed water.

In tanker on-loading, real-time measurement of the oil, water, and air content of the oil could be made while the oil is being loaded into the tanker. This would eliminate any need for settling time of the water and eliminate legal disputes over excess water content in the oil. In refinery monitoring, real-time measurement of water content and refinery oil can be made, thus permitting warning or automatic shut-off of downstream processes which would otherwise be harmed by large slugs of water occurring the pipelines.

Another application would be as a furnace monitor. It is known that oil-burning furnaces can explode if a globule of water is injected while the furnace is burning. The cost of repair to such a system is many times the cost of oil monitor warning system according to the present invention.

An additional application would be monitoring of interfaces between different fluids in pipelines. Transcontinental pipelines transmit a variety of fluids in the same pipeline by loading first one fluid and then another in a sequential manner. It is very important to be able, at a downstream pumping or switching station, to measure when these interfaces occur, and to determine over what distance mixing and contamination of the fluids has occurred.

The present invention has been described above in terms of several exemplary embodiments. These embodiments have been described merely for the sake of elucidating the concepts underlying the invention. The description of specific embodiments should not be construed as a representation that only those embodiments are within the scope of the invention. Conversely, the fact that a particular embodiment has not been described should not be construed as an indication that that embodiment is not within the scope of the present invenion. Instead, the invention should be regarded as being fully commensurate in scope with the following claims, properly construed in accordance with the dictates of the applicable patent laws.

What is claimed is:

1. Apparatus for measuring a volume fraction of a first fluid having a microwave radiation energy absorption peak at a predetermined microwave peak frequency in a mixture of said first fluid and a second fluid flowing through a three dimensional conduit, said apparatus comprising:
    first means, arranged on one side of a volume of said mixture, for generating a first microwave beam proximate said peak frequency, a second microwave beam below said peak frequency and a third microwave beam above said peak frequency;
    second means, arranged across said volume from said first means, for receiving said first, second and third generated microwave beams after they have passed through the mixture, and for generating a first signal indicative of attenuation of said first, second and third microwave beams in said mixture; and
    third means, electrically connected to said second means and responsive to said first signal, for computing said volume fraction of said first fluid in said mixture based on said first signal.

2. An apparatus as claimed in claim 1 wherein said first means comprises a microwave transmitter and a transmit horn, the transmit horn being arranged adjacent said volume.

3. An apparatus as claimed in claim 1 wherein said second means comprises a microwave receiver and a receive horn, said receive horn being arranged adjacent said volume.

4. An apparatus as claimed in claim 1 wherein the first fluid is water and said peak frequency is approximately 23 GHz.

5. Apparatus as claimed in claim 1 wherein said third means comprises a microcomputer.

6. Apparatus as claimed in claim 1 wherein said first fluid is water, said first frequency is $v_1$, said second frequency is $v_2$ and said third frequency is $v_3$ and said third means computes the volume fraction of said water according to the formula:

$$V_w = \frac{2av_1 - av_2 - av_3}{2a\omega v_1 - a\omega v_2 - a\omega v_3}$$

where $v_w$ = the volume fraction of water;
$av_1$ = measured average absorption at frequency $v_1$;

$av_2$=measured average absorption at frequency $v_2$;
$av_3$=measured average absorption at frequency $v_3$;
$awv_1$=absorption of water in droplet form at frequency $v_1$;
$awv_2$=absorption of water in droplet form at frequency $v_2$; and
$awv_3$=absorption of water in droplet form at frequency $v_3$.

7. Apparatus as claimed in claim 1 wherein said second means comprises a first receiving element responsive only to said first microwave beam and a second receiving element, displace from said first receiving element in a first direction parallel to a wavefront of said first microwave, responsive only to said second microwave beam.

8. Apparatus as claimed in claim 6 wherein said first means produces N distinct microwave beams, N being an integer greater than two, and wherein said second means comprises a linear array of N microwave receiving elements extending in said first direction, each responsive to a different one of said N microwave beams.

9. Apparatus as claimed in claim 8, wherein said first means comprises a linear array of N transmitting elements extending in said first direction.

10. Apparatus as claimed in claim 6 wherein said first means comprises a linear array of N transmitting elements extending in said first direction.

11. Apparatus as claimed in claim 10 wherein said each of said N transmitting elements produces microwave beams having at least two different frequencies.

12. An apparatus as claimed in claim 1, wherein said first fluid is water and said second fluid is oil.

13. The apparatus of claim 1, further comprising:
fourth means arranged adjacent said first means for generating fourth, fifth and sixth microwave beams, said fourth beam having a frequency proximate to but distinct from said first frequency, said fifth beam having a frequency proximate to but distinct from said second frequency, and said sixth beam having a frequency proximate to but distinct from said third frequency;
fifth means arranged adjacent said second means, for receiving said fourth, fifth and sixth beams after they have passed through said mixture, and for generating a second signal indicative of attenuation of said fourth, fifth and sixth beams in said mixture; wherein said third means is further operable for computing the locational distribution of said first fluid in said second fluid based on said first and second signals.

14. The apparatus of claim 13, wherein, said first, second and third beams define a first path through said mixture from said first means to said second means, said fourth, fifth and sixth beams define a second path through said mixture from said fourth means to said fifth means, wherein, said first path is parallel to and distinct from said second path.

15. The apparatus of claim 13, further comprising;
seventh means for generating seventh, eighth and ninth microwave beams, each of said beams having a frequency distinct from said first through sixth beams and distinct from one another;
eighth means for receiving said seventh, eighth and ninth beams, arranged across said volume from said seventh means so that said seventh, eighth and ninth beams define a third path non-parallel to said first and second paths, and for generating a third signal indicative of attenuation of said seventh, eighth and ninth beams in said mixture.

16. The apparatus of claim 15, wherein, said third means utilizes said first, second and third signals to compute said locational-distribution of said first fluid.

17. A method for measuring the volume fraction of a first fluid having a microwave energy absorption peak at a predetermined peak microwave frequency, in a mixture of said first fluid and a second fluid flowing in a three dimensinal conduit, said method comprising the steps of:
(a) generating a first microwave beam proximate said peak frequency, a second microwave beam below said peak frequency, and a third microwave beam above said peak frequency;
(b) transmitting said first second and third microwave beams through a volume of said mixture;
(c) receiving said transmitted first, second and third microwave beams;
(d) determining the attenuation of said first, second and third microwave beams;
(e) producing a signal indicative of said attenuation; and
(f) computing said volume fraction of water on the basis of said signal.

18. A method as claimed in claim 17 where said receiving step comprises receiving said first microwave at a first location said second microwave at a second location and said third microwave at a third location, each displaced from said first location in a direction parallel to the wavefront of said first second and third microwaves.

19. Apparatus for measuring a volume fraction of a first fluid in a mixture of said first fluid and a second fluid, said apparatus comprising:
first means, arranged adjacent a volume of said mixture, for generating first and second broad and coincident microwave beams of different frequencies;
second means, arranged across said volume from said first means, for receiving said first and second microwave beams after they have passed through the mixture, and for generating a first signal indicative of attenuation of said first and second microwave beams in said mixture;
third means, arranged adjacent said volume, for generating at least two additional microwave beams narrower than said first and second microwave beams and distinguishable from said first and second microwave beams by one of frequency, path, or timing;
fourth means, arranged across said volume from said third means, for receiving said additional microwave beams, and for generating a second signal indicative of whether said mixture blocked propagation of any of said additional microwave beams; and
computing means, responsive to said first signal and said second signal, for determining the volume fraction and distribution of said first fluid in said mixture.

20. A method for measuring the volume fraction and the locational distribution of a first fluid in a mixture of said first fluid and a second fluid, comprising the steps of:
transmitting a first microwave beam along a first path through said mixture;
transmitting a second microwave beam along a second path through said mixture, said first and second paths being essentially perpendicular to each other;
determining the attenuation of said first and second beams; and
computing said volume fraction and said locational distribution from said determination.

* * * * *